United States Patent [19]

Malek Afzali

[11] 4,220,163
[45] Sep. 2, 1980

[54] TIBIAL TORSION MEASURING DEVICE

[76] Inventor: Saeed Malek Afzali, 2233 Foxbourne, Toledo, Ohio 43614

[21] Appl. No.: 893,052

[22] Filed: Apr. 3, 1978

[51] Int. Cl.² .............................................. A61B 5/10
[52] U.S. Cl. .................... 128/782; 128/774
[58] Field of Search ........... 128/2 S, 2 R, 3 A, 143 C, 128/143 J, 143 K, 774–782; 33/174 D, 3 R, 3 B, 3 C, 174 R, 174 C; 73/172

[56] References Cited
U.S. PATENT DOCUMENTS 3,726,015  4/1973  Neumann ...................... 33/174 D X
4,062,355  12/1977  Kaye ............................. 33/174 D X

FOREIGN PATENT DOCUMENTS 360914  11/1931  United Kingdom ...................... 33/3 C
458313  12/1936  United Kingdom ...................... 33/3 C Primary Examiner—Robert W. Michell
Assistant Examiner—Jeffrey W. Tayon
Attorney, Agent, or Firm—Kenneth F. Cherry

[57] ABSTRACT

A device allowing direct measurement of tibial torsion. This mechanical device utilizes two hinged members and an angle measuring means to directly ascertain the amount of torsion of the tibia in the coronal plane.

1 Claim, 3 Drawing Figures

TIBIAL TORSION MEASURING DEVICE

BRIEF SUMMARY OF INVENTION

A measuring device which provides an easily reproducable clinical standard for the evaluation of the extent of tibial torsion is presented herein. Two moveable arms with indicators are attched to a common member and by proper manipulation of the arms and positioning device attached thereto a measurement of tibial torsion can be obtained. Angular and linear measurements of the position of the malleoli are made with this invention and thereby provide a reliable clinical standard by which to judge the extent of tibial torsion.

BACKGROUND OF THE INVENTION

Tibial torsion is the twist in the bone of the tibia itself. This is distinct from the rotation of the limb which takes place at the hip joint. Traditionally direct measurement of the torsion is accomplished through the use of x-ray shadows or various instruments which require estimates and judgement so that measurements may vary depending on the researcher's competence. Heretofor accurate, reproducable measurements of this type could only be acquired by direct measurement of anatomic specimens. Thus the measurements necessary to monitor the progress of treatment and to evaluate the propriety and extent of surgical correction could not be easily obtained.

Tibial torsion, femoral torsion and metatarus adductus are the primary causes of pigeon-toes. The lack of a reliable reproducable standard has hindered physicians in the evaluation of the extent of tibial torsion. Whereas the various aspects of bone deformities comprise a complex science which requires volumes of explanation an initial point of reference is suggested: "Pediatric Clinics of North America"—Vol. 17 No. 2 May, 1970.

DETAILED DESCRIPTION OF THE INVENTION

Figure 1:
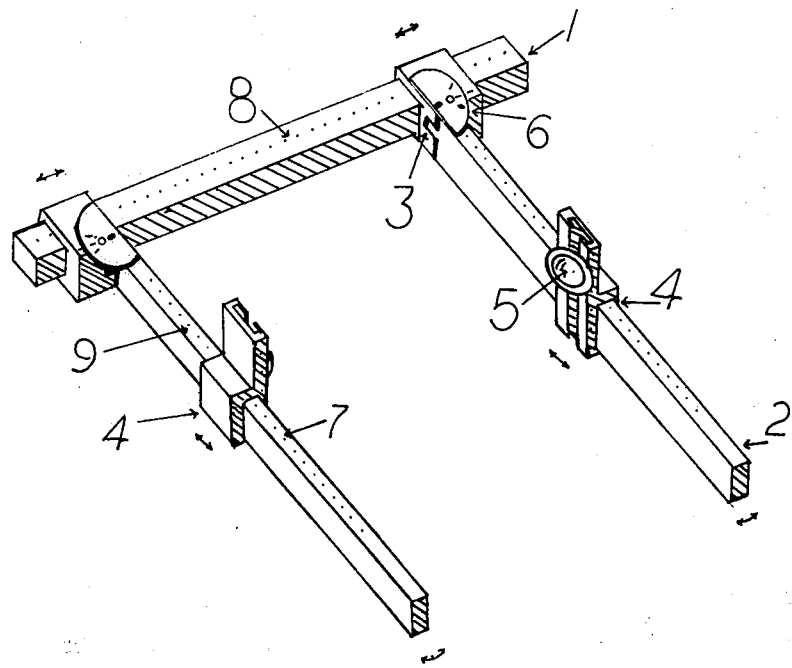
FIG. 1 is a view of one possible configuration of the invention.

To better understand the invention reference numerals to the drawings are used.

A device and method to ascertain the extent of Tibial Torsion has been invented. The device comprises a straight support member (1) which serves as the support for the other members. Mounted on the support member is a hinged member (2) having a means to ascertain the angular relationship (6) between the support member and hinged member. The means of ascertaining the angle may take several forms including a protractor type scale as shown or a separate angle measuring device or other combination to measure the angle formed. A hinged block (3) is the preferred mounting means.

On said hinged member a movable cup (5) like structure can be mounted. This cup can move along the hinged member on a mounting (4) and may be provided with the capability of also being positioned at various elevation as shown.

A second hinged member (7) with the same basic structure as the above discussed hinged member is also attached to the support member. This second hinged member is positioned so the cup like devices on both hinged members have the concave surface of the cups facing each other.

Appropriate linear and angular scales (8,9) can be on the various members of the device. A scale on the support member can indicate the distance between the hinged members. Also the relative position of the cup structure in both the horizontal and vertical planes can be measured.

A better understanding of the device can be obtained through the following example which refers to the accompanying drawings.

(1). The physician first examines the patient to determine the overall condition of the leg and foot bone structure.

(2). The foot is placed on a flat surface.

(3). With the support member of the invention behind the foot, the invention is positioned so the hinged members are both perpendicular to the support member. The cups are positioned to fit over the medial and lateral malleoleus.

(4). With the hinged members perpendicular to the support using either scales imprinted on the invention or a separate ruler the distance from the supportive member to the malleoli as well as the height of the malleoli above the flat surface can be established as shown by A & B of FIG. 2 with $\theta = 90°$.

Figures 2, 3:
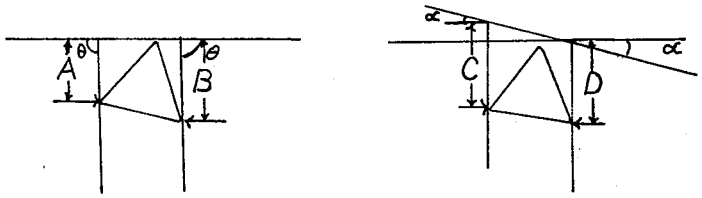
FIG. 2 depicts the geometric principal involved with a triangle used to depict tibial torsion.
FIG. 3 depicts the geometric principal of measuring tibial torsion relative to the position shown in FIG. 2.

(5). Next one of the cups, preferrable the one nearest the supportive structures is relocated on the hinged member so the distance between the supportive member and either cup is the same. i.e. C and D of FIG. 3 are equal.

(6). The hinged members are then manipulated so that the cups are placed over the malleoli.

(7). The extent of Tibular Torsion is indicated by the angle either hinged member forms with the supportive member since the angles are the same. This angle is measured either with a scale attached to the invention or a separate device. Angle $\alpha$ of FIG. 3 shows the measured angle.

Among the considerations in constructing the invention is either sufficient friction in the parts or a locking means to ensure sufficient rigidity for taking measurements. Also a soft insulating cover for the metal parts which may come in contact with the patient is advisable for patient comfort.

It has been found that a separate straight member can be used to ensure the hinged members are parallel and the separate member may also be graduated to assist in taking various measurements. In use this straight member is placed over the free ends of the hinged members.

Having described the invention I claim:

1. A device for measuring tibial torsion comprising a supportive member having attached thereto on moveable hinged supports at least two hinged members, said hinged members having thereon angle-measuring scales to show the angle between said hinged members and said supportive member, said hinged members having adjustably attached to each at least one positionable cup like structure for placement over the malleoli, said cup like structures to be fastened to said hinged members so that one of the cup like structures can be positioned over the malleoli when said supportive member is placed behind a patient's heel and the respective hinged member is at 90° to said supportive member, said hinged member having on each similar distance scales to ascertain the position of said cup like structure on said hinged member relative to said supportive member, further, the similar distance scales placed to allow the second cup like structure to be positioned precisely the same distance from said supportive member, further, when both said cup like structures are positioned the same distance from said supportive member when said hinged members are 90° to a said supportive member, and said cup like structures are then placed over a patient's malleoli without changing their respective positions on said hinged members, said measuring scales show the extent of tibial torsion.

* * * * *